United States Patent [19]

Carpenter et al.

[11] Patent Number: 5,256,706
[45] Date of Patent: Oct. 26, 1993

[54] CROSS-LINKAGE SURFACE-MODIFED MICACEOUS PARTICULATES AND COATING COMPOSITIONS CONTAINING THE SAME

[75] Inventors: Clint W. Carpenter, Plymouth; Thomas G. Savino, Northville, both of Mich.

[73] Assignee: BASF Corporation, Southfield, Mich.

[21] Appl. No.: 900,803

[22] Filed: Feb. 11, 1991

Related U.S. Application Data

[63] Continuation of Ser. No. 386,376, Jul. 27, 1989, Pat. No. 5,013,770.

[51] Int. Cl.$^5$ .............................................. C08K 9/06
[52] U.S. Cl. .................... 523/213; 523/216; 524/437; 524/449; 556/419; 556/420
[58] Field of Search ............... 523/213, 216; 524/449, 524/437; 556/419, 420

[56] References Cited

U.S. PATENT DOCUMENTS

| | | | |
|---|---|---|---|
| 4,591,652 | 5/1986 | DePasquale et al. | 556/419 |
| 4,670,421 | 6/1987 | DeVries et al. | 556/419 |
| 4,714,770 | 12/1987 | Hsu et al. | 556/419 |

Primary Examiner—Paul R. Michl
Assistant Examiner—Edward Cain
Attorney, Agent, or Firm—Rupert B. Hurley, Jr.; Paul L. Marshall

[57] ABSTRACT

Compounds useful for improving the intra-film binding of micaceous particulates in films formed from coating compositions which contain such micaceous particulates comprise urethanes or ureas which are the reaction products of silylalkyl- or silylaryl isocyanates with blocked or unblocked alcohols, aminoalcohols, or polydiol alcohols. The compounds may also be the reaction products of silylalkyl- or silylarylamines with half-blocked diisocyanates which are themselves the reaction products of a diisocyanate with a blocked or unblocked alcohol, aminoalcohol, or polydiol alcohol.

Micaceous particulates which have been surface modified by reaction with these compounds, as well as coating compositions comprising such surface-modified micaceous particulates, and coated substrates are also disclosed.

21 Claims, No Drawings

CROSS-LINKAGE SURFACE-MODIFED MICACEOUS PARTICULATES AND COATING COMPOSITIONS CONTAINING THE SAME

This is a division of application Ser. No. 07/386,376 filed Jul. 27, 1989 now U.S. Pat. No. 5,013,770.

TECHNICAL FIELD OF THE INVENTION

The present invention relates to decorative coating compositions primarily suited for use in the field of automotive coating. More particularly, this invention concerns compounds useful for surface modification of micaceous particulates for use in automotive coating systems, to surface-modified micaceous particulates, to coating compositions containing such surface-modified micaceous particulates, and to substrates coated with such coating compositions.

BACKGROUND OF THE INVENTION

Recent years have seen the introduction of multi-layer or multi-coat paint systems for metal and plastic substrates, particularly automotive products. Automotive multi-coat systems generally begin with a protective primer coat which is applied by conventional electrocoating processes directly onto a phosphatized or otherwize pretreated automotive body. This electrocoat layer is then typically coated with a primer/surfacer coating, followed by one or more layers of pigmented base coat. While the pigmented base coat may in some cases serve as the finish coat, often a final clear, unpigmented, protective top coat layer is applied over the base coat to provide durability, gloss, depth of color, and distinctness of image to the finished coating. In multi-layer coating systems, the pigmented basecoat is often quite thin, being of the order of 0.5 to 1.0 mils (0.0013 to 0.0025 cm) thickness, while the protective clear top coat is thicker, generally of the order of 2 to 3 mils (0.0051 to 0.0076 cm) thickness.

In recent years, so-called "metallic" effect colors have found wide acceptance among automobile buyers. These metallic effects in automotive finishes are generally achieved by incorporating highly reflective, finely divided particulates into the pigmented base coat of a multi-layer coating system. The particulates are generally aluminum flake, mica particles, or mica particles which have been encapsulated or coated with a metal oxide, typically iron oxide or titanium dioxide. The presence of finely divided reflective particulates in the cured base coat layer produces a metallic sparkle effect which is popular with the automotive consuming public.

While the introduction of "high tech" multi-layer automotive coatings, particularly the metallic color styles, has found wide acceptance in the automotive consuming public, such complex coating systems are not without some associated problems. Not least of these is the problem of producing a total coating system which has the requisite durability and resistance to the damaging effects of weather, ultraviolet light and environmental pollutants.

For example, in a typical "metallic" multilayer coating system, there may be as many as five interlayer interfaces between the substrate car body and the clear top coat: 1) the clear top coat to pigmented basecoat interface; 2) the base coat to metallic or mica flake interface; 3) the basecoat to primer-surfacer interface; 4) the primer-surfacer to electrocoat interface; and 5) the electrocoat to vehicle body interface. The potential exists for delamination or adhesive failure at one or more of these interfaces as a result of weathering or other environmental stress. Sometimes this can be a particular problem in base coat layers which contain metallic flake or mica flake materials. Hydroxyl functions on the metal or mica particle surfaces provide sites for hydrogen bonding of water which finds its way into the base coat as a result of normal weathering processes. This trapping of water can serve to exacerbate the problem of delamination of the base coat layer where the bonding between the metal flake or mica flake particles and the surrounding polymer film matrix is, at best, already weak.

There is thus a need in the automotive coatings art for a means of increasing the weatherability and durability of automotive finishes which contain metallic or mica particulates.

SUMMARY OF THE INVENTION

The present invention provides, in one aspect a class of compounds for use in surface modification of micaceous particulates to improve the bonding of such particulates into films formed from film-forming coating resins. By the term "micaceous particulates" as used throughout this specification and the appended claims is meant particulate materials comprising mica, and metal oxide coated or encapsulated micas. The class of surface modifying compounds of this invention have the general formula

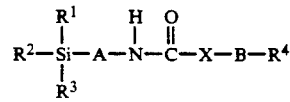

where $R^1$, $R^2$, and $R^3$ may be the same or different and are selected from alkyl of from one to ten carbon atoms, alkoxyl of from one to ten carbon atoms, alkoxyalkoxyl of from two to ten carbon atoms, alkanoyloxy of from two to ten carbon atoms, or halogen, with the proviso that $R^1$, $R^2$, and $R^3$ may not all be alkyl. The group "A" is a divalent radical selected from straight or branched alkylene of from one to twelve carbon atoms, phenylene or phenylene substituted with halogen, or alkyl or alkoxyl of from one to four carbon atoms. The group "X" is a divalent radical selected from either —O— or —NH—.

The group "B" is a direct valence bond or is a group having the formula

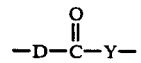

wherein D is a diisocyanate moiety and Y is a divalent radical selected from —O— or —NH—. As used throughout this specification and the appended claims, the term "diisocyanate moiety" denotes the residue remaining after the hypothetical removal of both isocyanate functional groups from a diisocyanate compound.

The group $R^4$ is

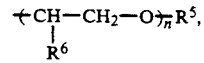

and n is an integer of from zero to one hundred. The group $R^6$ is hydrogen, alkyl of from one to eight carbon atoms, or

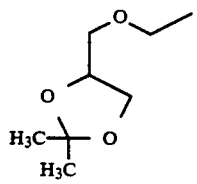

and $R^5$ is a polyol of from two to twenty carbon atoms having one or more hydroxyl groups in which the hydroxyl group or groups have been blocked by reaction with a suitable hydroxyl protecting group.

In all of the above formulae, it is to be understood that the carbon free-valence bond of the group "—D—COY—" is attached to the group designated "X" and the free-valence bond of Y is attached to the group designated $R^4$.

As used throughout this specification and the appended claims, the term "alkyl" denotes a monovalent hydrocarbon radical derived by the hypothetical removal of a single hydrogen atom from a branched or unbranched chain saturated hydrocarbon molecule, for example, methyl, ethyl, propyl, iso-propyl, etc. The term "alkoxyl" denotes a monovalent radical derived by the hypothetical removal of the hydroxyl hydrogen from a straight or branched chain alcohol, for example methoxyl, ethoxyl, etc. The term "cycloalkylene," denotes a carbocyclic ring such as cyclopentylene, cyclohexylene, and the like which may optionally be substituted with alkyl of from one to six carbon atoms. The term "phenylene" denote divalent radicals derived by the hypothetical removal of two hydrogen atoms each from cyclopentane, cyclohexane, or benzene. The term "alkoxylalkyl" denotes a monovalent radical derived by the hypothetical removal of a hydrogen atom from an ether, for example groups such as ethoxyethyl ($CH_3CH_2OCH_2$—). The term "alkoxylalkoxyl" denotes a monovalent radical derived by the hypothetical removal of the hydroxyl hydrogen from a diol monoether, for example groups such as $CH_3CH_2OCH_2$—O—. The term "alkanoyloxy" denotes a monovalent radical derived by the hypothetical removal of the acidic hydrogen from a straight or branched carboxylic acid as, for example, groups such as acetyloxy ($CH_3COO$—). The term "alkylene" denotes a divalent radical derived by the hypothetical removal of two hydrogen atoms from a straight or branched chain saturated hydrocarbon.

In another embodiment of the present invention, there is provided a surface modified micaceous particulate material which comprises the product derived from treatment of mica or a metal oxide encapsulated mica with a compound described above. By the term "treatment" is meant contacting the mica or metal oxide coated or encapsulated mica with the surface treatment compound, with or without a solvent, with or without heating, followed by physical separation of the mica from any excess of the surface treatment compound by a suitable process such as filtration and subsequent heating to complete the reaction of the surface modifying compound with reactive groups on the surface of the mica particles.

Suitable micaceous materials utilizable in this embodiment of the invention are muscovite (potassium aluminum silicate) or phlogopite (magnesium aluminum silicate) micas or mixtures thereof or either of these types of mica or their mixtures which have been encapsulated in a metal oxide such as iron oxide or titanium dioxide (anatase or rutile). In addition, iron oxide coated micas which further contain absorption colorants in the coating may also be used. Materials of this type include iron oxide encapsulated micas which contain absorption colorants such as ferric ferrocyanide (C.I. 77510), and carmine (C.I. 75470).

These mica or metal oxide coated or encapsulated micas generally have particle sizes ranging in thickness of from about 0.3 $\mu$m to about 0.8 $\mu$m with the longest dimension of most platelets ranging from about 5 $\mu$m to about 90 $\mu$m. Micaceous particle platelets having their longest dimension in the range from about 5 $\mu$m to about 25 $\mu$m have a higher diffuse reflectance, producing finishes with a soft satin luster. Platelets having their longest dimension in the range of between about 10 $\mu$m to about 50 $\mu$m have high specular reflectance and produce finishes with highest luster. Those platelets having their longest dimension in the range of from about 10 $\mu$m to about 90 $\mu$m have low opacity and produce finishes with the best "sparkle" effect.

Particulate micas and metal oxide coated or encapsulated particulate micas suitable for use in producing the surface treated micas of this invention are described in "Nacreous (Pearlescent) Pigments and Interference Pigments," by L. M. Greenstein in The Pigment Handbook, Volume 1, Properties and Economics, Peter A. Lewis, Ed., John Wiley & Sons, New York, 1988, which is incorporated herein by reference. Micas and metal oxide encapsulated or coated micas are commercially available from a number of suppliers, including The Mearl Corporation, 41 East 42d Street, New York, N.Y. 10017 and EM Chemicals, 5 Skyline Drive, Hawthorne, N.Y. 10532.

In yet another embodiment of the present invention, there are provided coating compositions suitable for use as the base coat composition of a multi-layer coating system which comprise a film-forming resin, a cross-linking agent, a pigment, and a particulate micaceous material surface modified by treatment with a compound as described above.

In another embodiment of the present invention there are provided substrates coated with a cured film formed from coating compositions comprising a particulate micaceous material surface modified by treatment with a compound as described above. Suitable substrates include metals and plastics.

DETAILED DESCRIPTION

The compounds of the present invention are low molecular weight monomers or oligomers having at one end a reactive silyl functionality which is capable of hydrolyzing to produce functional groups capable of reacting with and bonding to oxygen functionalities on the surface of mica or metal oxide encapsulated mica particulates. The compounds comprise, at their other end a polyol group having at least one hydroxyl functionality. The hydroxyl group or groups are initially blocked by a group which can unblock to produce the free hydroxyl group or groups which are free to react with a cross-linking agent in any coating composition into which material is formulated.

Particular sub-classes of compounds falling within the scope of the present invention include those having the following structural formulae:

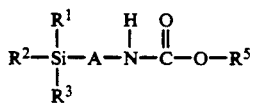

wherein A, R¹, R², R³, and R⁵ are as defined above;

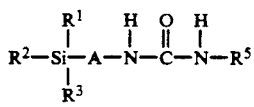

wherein A, R¹, R², R³, and R⁵ are as defined above;

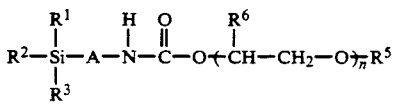

wherein A, n, R¹, R², R³, R⁵, and R⁶ are as defined above;

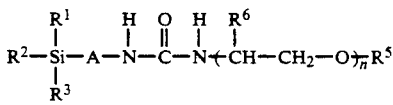

wherein A, n, R¹, R², R³, R⁵, and R⁶ are as defined above;

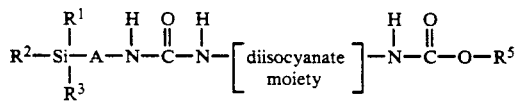

wherein A, R¹, R², R³, and R⁵ are as defined above, and "diisocyanate moiety" denotes a divalent radical derived from a diisocyanate compound of the group recited above by removal of the two isocyanate functionalities;

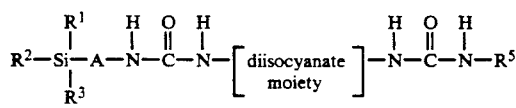

wherein A, R¹, R², R³, R⁵, and "diisocyanate moiety" are as defined above;

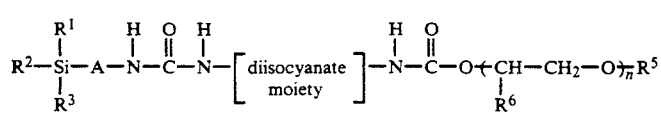

wherein A, n, R¹, R², R³, R⁵, R⁶, and "diisocyanate moiety" are as defined above, and

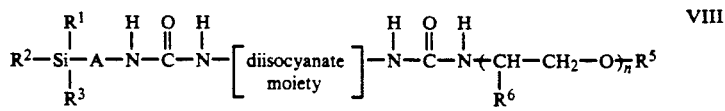

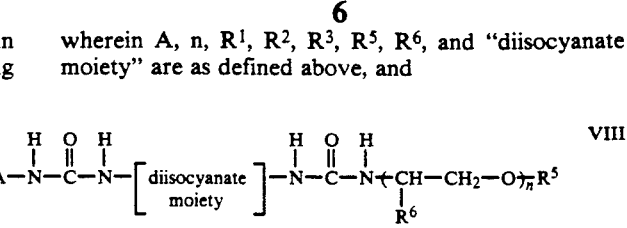

wherein A, n, R¹, R², R³, R⁵, R⁶, and "diisocyanate moiety" are as defined above.

Compounds of sub-classes I and II above are preferred, particularly for use in coating compositions comprising non-aqueous film-forming resins. Compounds of sub-class III, containing a polar poly(oxyalkylene) chain extension and thus greater water miscibility, are preferred for use with coating compositions based upon water-miscible film-forming resins.

Polyols suitable as starting materials for use in preparing compounds of this invention are straight chain or branched chain polyhydroxy compounds of from two to twenty carbon atoms. Preparation of the blocked polyols for use in preparing the compounds of this invention is considerably simplified, however, when the starting polyol is selected from diols such as ethylene glycol, propylene glycol, 1,2-, 1,3-, and 1,4-butanediol, 1,2-, 1,3-, 1,4-, 1,5-, and 1,6-hexanediol, and the like or polyols of from three to twenty carbon atoms in which two or more of the hydroxyl groups are attached to contiguous carbon atoms in a chain or ring (i.e. vicinal dihydroxy groups) or adjacent carbon atoms which are separated by one carbon atom in a chain or ring (i.e. 1,3-diol groups).

In the case of simple diols such as, for example 1,3-propanediol, the starting diol is reacted with a hydroxyl protecting group reagent to produce the half-blocked diol. This material is then subsequently used to prepare the compunds of this invention as detailed below. Compounds which contain 1,2-diol or 1,3-diol groups in addition to another hydroxyl functionality are first reacted with a hydroxyl function protecting reagent which is difunctional. A typical example is a ketal-producing reagent which protects 1,2-diols and 1,3-diols by forming a five- or six-membered ring, leaving the remaining hydroxyl functionality free for subsequent reactions. For example, reaction of glycerol with acetone produces the iso-propylidene ketal of glycerol, leaving the third hydroxyl group free.

As used throughout this specification and the appended claims, the terms "vicinal" dihydroxy groups will be used to denote 1,2-diol structures, and "adjacent" dihydroxy groups to denote 1,3-diol structures. The term "polydiol alcohol" denotes compounds where pairs of hydroxy groups are vicinal and/or adjacent and remaining hydroxy groups are separate or more or less remote in location on the molecule from these vicinal or adjacent dihydroxy groups.

Examples of such polydiol alcohols include, but are not limited to, the sugar alcohols such as glycerol, ribotol, arabitol, xylitol, and the like, as well as compounds such as 1,2,4-butanetriol, 1,2,5-pentanetriol, 1,3,5-pentanetriol, 1,2,6-hexanetriol, 1,3,6-hexanetriol and the like. The hexopyranoses or hexofuranoses, such as glucose and galactose, already in a cyclic acetal form, are readily converted by reaction with difunctional hydroxyl protecting reagents to materials which are useful in preparing compounds of this invention.

Suitable hydroxyl protecting group reagents and methods for their use in forming blocked hydroxyl groups (both single hydroxyl groups and vicinal and adjacent dihydroxyl groups) are disclosed in Chapter 2 of T. H. Greene, Protective Groups in Organic Synthesis, John Wiley & Sons, New York 1981, the teachings of which are incorporated herein by reference.

Diisocyanates suitable as starting materials for the synthesis of compounds according to this invention include diisocyanates in which the diisocyanate moiety comprises straight or branched alkylene of from two to six carbon atoms such as ethylene diisocyanate, 1,3-propylene diisocyanate, 1,4-butylene diisocyanate, 1,5-pentylene diisocyanate, 1,6-hexylene diisocyanate, 1,2-propylene diisocyanate, 1,2-butylene diisocyanate, 2,3-butylene diisocyanate, 1,3-butylene diisocyanate. Likewise, diisocyanates in which the diisocyanate moiety comprises cycloalkylene and substituted cycloalkylene of from five to twelve carbon atoms may be employed, such as cyclopentane diisocyanates, the cyclohexane diisocyanates, 2-methyl-1,5-cyclohexane diisocyanate, and isophorone diisocyanate. Diisocyanates in which the diisocyanate moiety comprises an aromatic ring system such as phenylene, substituted phenylene, naphthylenyl, and the like may also be used, such as 1,3-bis-(2-isocyanato-2-propyl)benzene ("TMXDI"), phenylene diisocyanate, 2,4-toluene diisocyanate, and 2,6-toluene diisocyanate, 1,4-naphthalene diisocyanate and 1,5-naphthalene diisocyanate. Likewise, the biphenyl and substituted biphenyl diisocyanates such as 4,4'-biphenyl diisocyanate, and the diarylalkylene diisocyanates in which two diisocyanate substituted phenyl groups are attached to an alkylene group such as methylene may also be used to prepare compunds of this invention. Examples of the latter include 4,4'-bis-(isocyanatophenyl)methane and the like.

GENERAL PREPARATIVE METHODS

Preparation of Compounds of Formula I

Compounds of formula I, above, are generally prepared by reacting a half-blocked diol or blocked polydiol alcohol with a silylalkyl or silylaryl isocyanate of formula IX

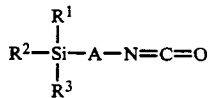

where A, $R^1$, $R^2$, and $R^3$ are as previously defined. The term "half-blocked diol" as used throughout this specification and the appended claims denotes a diol such as, for example, 1,3-propanediol which has been half-blocked by reaction with an equimolar amount of a monohydroxy protecting group. The term "blocked polydiol alcohol" as used throughout this specification and the appended claims denotes a polydiol alcohol compound as defined above in which the 1,2- or 1,3-dihydroxy groups are blocked by reaction with a difunctional hydroxy protecting group. A typical example of a block polydiol alcohol is glycerol, or 1,2,6-hexanetriol in which two of the vicinal hydroxy groups have been blocked, leaving the third hydroxyl group free.

In the case of a half-blocked diol starting material, the reaction is typified by the following where a compound of formula I is prepared from 1,3-propanediol which is blocked by reaction with chloromethyl methyl ether:

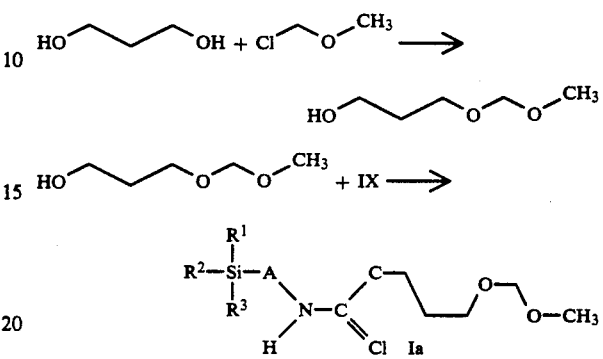

Reactions of the type where the starting material is a blocked polydiol alcohol are typified by the following in which the blocked polydiol alcohol compound is glycerol which has been previously blocked by reaction with acetone to form the iso-propylidene ketal:

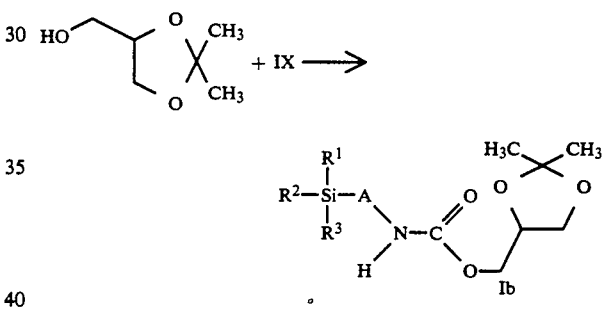

The reaction between the silylalkyl or silylaryl isocyanate and the half-blocked diol or the blocked polydiol alcohol is generally carried out by mixing equimolar amounts of the reactants, optionally, with a small amount of a condensation catalyst such as dibutyl tin dilaurate, and heating the mixture for a period of up to about eight hours to effect substantially complete reaction between the isocyanate and the alcohol. The course of the reaction is followed by infrared spectroscopic analysis and the reaction is stopped at the point where the isocyanate absorption band no longer appears in the infrared spectrum of the reaction mixture.

Compounds of formula IX are commercially available, or can be generally prepared by reaction of silyl-substituted amines of formula XV (vide infra) with carbon monoxide in the presence of palladium chloride catalyst. (See, for example, Stern and Spector, J. Org. Chem., 31: 596 (1966). The starting silyl-substituted amines are commercially available, for example from Petrarch Systems, Bartram Road, Bristol, Pa. 19007.

Compounds of formula IX where $R_1$, $R_2$, and $R_3$ are lower alkoxyl and A is alkylene, are available from Union Carbide Corp., 270 Park Avenue, New York, N.Y. 10017. A particularly preferred alkoxylsilylalkyl isocyanate of the type represented by formula IX above is 3-(trimethoxysilyl)propyl isocyanate, available from Union Carbide as Y9030.

Preparation of Compounds of Formula II

Similarly, compounds of formula II above are prepared by reacting the appropriate silylalkyl or silylaryl isocyanate of formula IX with an aminoalcohol of from two to twenty carbon atoms in which the hydroxy function has been blocked by reaction with a suitable monofunctional hydroxyl protecting group or a polydiol amine compound in which the 1,3- and/or 1,4-diol groups have been blocked by reaction with suitable difunctional hydroxyl protecting groups.

Alternatively, the aminoalcohol or polydiol amine can be reacted directly with the silylalkyl- or silylaryl isocyanate without prior protection or blocking of the hydroxyl groups because of the facility of reaction between the amino group and the isocyanate group. This alternative route to compounds of formula II affords savings in both time and cost of goods.

The reaction between the blocked or unblocked aminoalcohol or blocked or unblocked polydiol amine is generally carried out by charging the silylalkyl or silylaryl isocyanate to the reaction vessel and heating to a temperature of between about 40° C. to about 80° C., preferably about 60° C. The blocked or unblocked aminoalcohol or blocked or unblocked polydiol amine is then added slowly to the reaction vessel contents. Following addition of the amine compound, the resulting mixture is held at a temperature of between 40° C. and 80° C. for a period of up to one hour, or until the reaction is substantially complete. The course of the reaction is followed by infrared spectroscopic analysis and the reaction is stopped at the point where the isocyanate absorption band no longer appears in the infrared spectrum of the reaction mixture.

Preparation of Compounds of Formula III

Compounds of formula III above are generally prepared by first reacting the desired half-blocked diol or polydiol alcohol (in which the diol groups have been blocked by a suitable protecting group) with ethylene oxide, propylene oxide, or the desired substituted oxirane to produce a poly(oxyalkylene) alcohol (compound X) in accordance with the reaction scheme detailed below.

The intermediates of formula X are next reacted with the silylalkyl or silylaryl isocyanate of formula IX above by mixing equimolar amounts of the reactants with, optionally, a small amount of a condensation catalyst such as dibutyl tin dilaurate, and heating the mixture for periods of up to about eight hours or until the reaction is substantially complete. The course of the reaction is followed by infrared spectral analysis and the reaction is stopped at the point where the isocyanate absorption band no longer appears in the infrared spectrum of the reaction mixture.

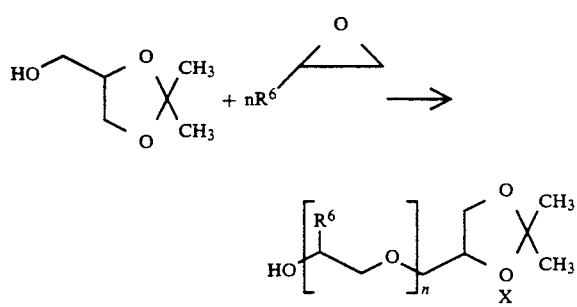

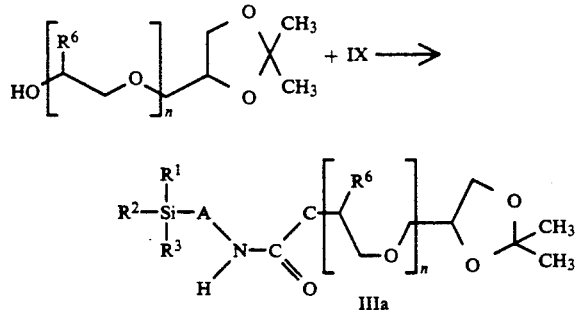

Preparation of Compounds of Formula IV

Compounds of formula IV are prepared in a manner similar to that described above for compounds of formula III. A blocked-hydroxyl poly(oxyalkylene) amine of formula XI is first prepared by a reaction between the desired half-blocked diol or a polydiol alcohol (in which the diol groups have been blocked by a suitable protecting group) and ethylene oxide, propylene oxide, or the desired oxirane as described above until the desired average molecular weight of the polymer is achieved. Then an aziridine (typically propylene aziridine) is added to the reaction mixture to terminate the growing polymer chains with an amine functionality.

The blocked-hydroxyl poly(oxyalkylene) amine of formula XI is then reacted with the silylalkyl or silylaryl isocyanate of formula IX above to produce the compounds of formula IV where n ranges between 1 and about 100, preferably between about 30 and about 60. This reaction is generally carried out in an inert, aprotic organic solvent at a temperature of from about 40° C. to 60° C. for a period sufficient to bring about substantially complete reaction between the starting materials. As described above, the course of the reaction is followed by infrared spectral analysis until there is no further indication of the presence of isocyanate functionality.

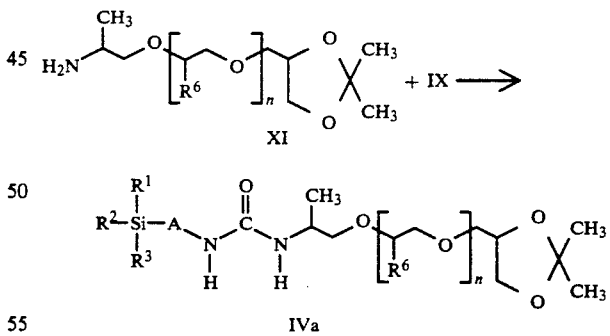

Preparation of Compounds of Formula V

The compounds of formula V above are prepared by first reacting the desired diisocyanate with the desired half-blocked diol or a polydiol alcohol (in which the diol groups have been blocked by a suitable protecting group) to produce a half-blocked isocyanate (compound XII).

This reaction is generally carried out by first dissolving the desired diisocyanate compound in an inert, aprotic solvent such as dichloromethane and heating to a temperature of between ambient and about 60° C., preferably about 40° C. An equimolar amount of the half-blocked diol or blocked polydiol alcohol compound is then slowly added, after which the temperature is maintained at between ambient and about 60° C. overnight.

A silylalkyl- or silylarylamine of formula XV is then added slowly to the reaction mixture, maintaining the temperature between ambient and about 60° C., preferably about 40° C. for about one hour or until infrared spectroscopic analysis indicates the absence of isocyanate groups, after which the solvent is removed by distillation.

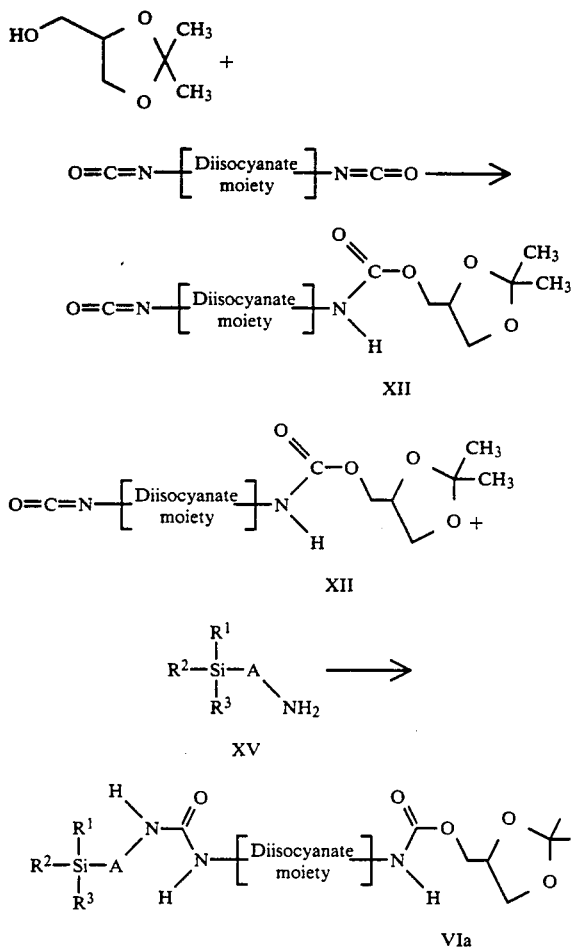

Preparation of Compounds of Formula VI

The compounds of formula VI above are generally prepared by first reacting the desired blocked aminoalcohol or blocked polydiol amine with the desired diisocyanate to form the half-blocked diisocyanate compound. Alternatively the aminoalcohol or a polydiol amine in which the hydroxyl groups are not blocked are reacted with the desired diisocyanate to produce the half-blocked diisocyanate.

This reaction is carried out in a suitable low-boiling, inert, aprotic solvent such as pentane or hexane at a temperature of about −78° C. The diisocyanate compound is dissolved in the solvent, the mixture is cooled, and an equimolar amount of the blocked or unblocked aminoalcohol or blocked or unblocked polydiol amine is slowly added. The mixture is allowed to react for a period of about eight hours or until the reaction is substantially complete. The mixture is allowed to warm to ambient temperature, and the silylalkyl- or silylarylamine compound is slowly added to the mixture. The ensuing reaction is allowed to proceed until infrared spectroscopic analysis indicates the absence of isocyanate functionality. The solvent is removed to recover the compound of formula VI.

Preparation of Compounds of Formula VII

The compounds of formula VII above are generally prepared by first forming a poly(oxyalkylene) alcohol of formula X above and then adding one mole of the polyether alcohol to at least one mole of the desired diisocyanate of formula XII to form a half-blocked diisocyanate. The half-blocked diisocyanate is subsequently reacted with the silylalkyl- or silylarylamine of formula XIV to form the compounds of formula VII above. These reactions are generally carried out under the conditions described above.

Preparation of Compounds of Formula VIII

The compounds of formula VIII are generally prepared by first preparing a blocked-hydroxyl poly(oxyalkylene) amine as detailed above under the section describing the preparation of compounds of formula IV. The blocked-hydroxyl poly(oxyalkylene) amine is next reacted with the desired diisocyanate to form the half-blocked diisocyanate which is subsequently reacted with the silylalkyl- or silylaryl amine of formula XIV to form the compounds of sub-formula VIII. Alternatively the unblocked aminoalcohol or unblocked poly(diol) amine may be first reacted with the diisocyanate to form the half-blocked diisocyanate, followed by reaction of the product of that reaction with the silylalkyl- or silylarylamine. These reactions are generally carried out under the conditions described above.

Preparation of the Surface-Modified Micaceous Particles

The surface modifying compound, prepared according to one or more of the methods detailed above, is used to treat the surface of a micaceous particulate material. The surface treatment compound of formulae I through VIII above, or any mixture thereof, is dissolved in water or a wet (i.e. water-containing) alcohol such as methanol, ethanol, propanol, and the like. Water-containing alcohols are the preferred solvents for this process because of the ease with which the mica particulate disperses without undesired caking or agglomeration in such solvent systems. The pH of the mixture is adjusted to about pH 4.5 to about pH 5.5 by the addition of an organic acid such as acetic acid. The function of the water and acid is to hydrolyze the groups attached to the silicon atom in the surface modification compound. Under these conditions, the hydroxyl blocking group(s) hydrolyze only slowly, so the principal reaction is that of hydrolyzing the substituents on the silicon atom.

While not adhering to any particular theory to the exclusion of others, it is believed that the water contained in the alcoholic solvent converts the reactive groups attached to the silicon atom of the surface modification compound to hydroxyl groups. For this reason, the three groups $R^1$, $R^2$, and $R^3$, attached to the silicon atom in the surface modifying compound may not all be alkyl, which are resistant to hydrolysis under these conditions. While one or two of the substituent groups may be alkyl, it is necessary that at least one of the substituent groups attached to the silicon atom be alkoxyl, alkoxylalkoxyl, alkanoyloxy, or halogen.

The hydroxyl groups which result from hydrolysis of the substituent groups on the silcon atom then react with hydroxyl groups on the surface of the micaceous particulate material to form —Si—O—M— bonds where M represents the surface metal on the micaceous particulate material (silicon, iron or titanium). It is believed that the surface modification which results from the treatment of the micaceous particulate material with the compounds of the present invention involves the direct covalent bonding of the surface modification compound to the micaceous particles through the —Si—O—M— bonds which form. However, the exact nature of the interaction of the surface modification compounds and the micaceous particulate material is not known exactly at the time of filing of this application. Therefore, throughout this specification and the appended claims, the terms "surface modification" and "surface modified" will be used to denote the interaction and resulting composition when micaceous particulates are treated with the compounds of the present invention of formulae I-VIII above by the method just described.

The amount of water present in the wet alcohol solvents ranges between a minimum amount effective to bring about such hydrolysis, typically about five percent, to an upper limit of essentially alcohol-free water. The micaceous particulate material is then added to the aqeuous alcoholic solution of the surface modification compound, and the mixture slurried for ten to fifteen minutes and then filtered. The filtered material is dried and cured by heating at about 100° C. to about 150° C., preferably at about 110° C. to about 120° C. for a period of from about one hour to about twelve hours. The heating or curing step is believed to be necessary to effect bonding between the surface modifying compound and the micaceous material. The surface modified micaceous particulate material is then ready for incorporation into a coating formulation, or may be stored for later use.

These materials are characterized by the presence of blocking groups still remaining on the hydroxyl functionality of the surface treatment compounds; hence these materials are particularly adapted for use in water-borne coating systems where hydrolysis and deblocking will occur naturally due to the action of water present in the water-borne coating compositions. In those instances where the surface modified micaceous particulates are to be used in a solvent-borne coating system, the treated mica may optionally be partially or completely unblocked following the heating or curing step and prior to incorporation of the treated mica particulates into the coating composition. This is accomplished by using deblocking reagents and conditions suited for the particular blocking group(s) as detailed in Chapter 2 of Greene, Protective Groups in Organic Synthesis, cited above.

For example, in the case of blocking groups such as acetals, ketals, and the like which are subject to acidic hydrolysis, the surface modification compound may be subjected to longer periods of hydrolysis in aqueous acidic media at the point prior to contacting the compound with the mica particulates. This longer period of hydrolysis serves to hydrolyze the substituents on the silicon atom as well as the groups blocking the hydroxyl functionalities. The product of this hydrolysis is then contacted with the mica material and cured as described above to produce the surface modified mica particulate material. This material, having the unblocked hydroxyl functionality, is suitable for incorporation into solvent-borne coating compositions.

Preparation of Coating Compositions

Coating compositions of the present invention are formulated by mixing the surface modified micaceous particulates of the present invention, along with other components, into suitable coating compositions which are sprayed or electrostatically deposited onto metal or plastic substrates such as, for example, automotive vehicle bodies.

Suitable film forming materials for use in formulating the coating compositions of this invention include acrylics, alkyds, polyurethanes, polyesters and aminoplast resins. These film-forming resins systems may be solvent borne, employing conventional volatile organic solvents such as aliphatic, cycloaliphatic and aromatic hydrocarbons, esters, ethers, ketones and alcohols including such things as toluene, xylene, butyl acetate, acetone, methyl isobutyl keyone, butyl alcohol, etc. Alternatively, water-borne film-forming resin systems may be employed as well.

When using solvent-borne film-forming resins as the principal resin of the coating composition, it is preferred that the surface-modifying compounds of this invention are of formulae I, II, V, and VI above which lack a poly(oxyalkylene) chain-extending moiety. These compounds and the corresponding surface modified mica particulates possess greater miscibility with solvent-borne coating systems. In water-borne coating systems, the preferred surface-modifying compounds of this invention are of formula III, IV, VII, and VIII which contain a poly(oxyalkylene) chain extending group which enhances the water miscibility of the compounds and the corresponding surface-modified mica particulates.

In coating systems employing volatile organic solvents, although it is not required, it is preferred to include from about 2% to about 50% by weight of a cellulose ester and/or wax (e.g. poly-ethylene) which facilitates quick release of the volatile organic solvent resulting in improved flow or leveling out of the coating. The cellulose esters used must be compatible with the particular resin systems selected and include such things as cellulose nitrate, cellulose propionate, cellulose butyrate, cellulose acetate butyrate, cellulose acetate propionate, and mixtures thereof. The cellulose esters when used are preferably used in about 5% to about 20% by weight based on film forming solids. The acrylic resins in the base coat may be either thermoplastic (acrylic lacquer systems) or thermosetting. Acrylic lacquers such as are described in U.S. Pat. No. 2,860,110 are one type of film forming composition useful according to this invention in the base coat. The acrylic lacquer compositions typically include homopolymers of methyl methacrylate and copolymers of methyl methacrylate which contain among others, acrylic acid, methacrylic acid, alkyl esters of acrylic acid, alkyl esters of methacrylic acid, vinyl acetate, acrylonitrile, styrene and the like.

Another type of film forming material useful in forming the base coat of this invention is a combination of a cross-linking agent and a carboxy-hydroxy acrylic copolymer. Monomers that can be copolymerized in the carboxy-hydroxy acrylic copolymer include esters of acrylic and methacrylic acid with alkanols containing 1 to 12 carbon atoms, such as ethyl acrylate, methyl methacrylate butyl acrylate, butyl methacrylate, 2-ethylhexyl acrylate, lauryl methacrylate, benzyl acrylate, cyclohexyl methacrylate, and the like. Additional monomers are acrylonitrile, methacrylonitrile, styrene, vinyl toluene, α-methyl styrene, vinyl acetate, and so forth. These monomers contain one polymerizable ethylenically unsaturated group and are devoid of hydroxyl and carboxylic groups.

The cross-linking agents used in combination with the hydroxy-carboxy copolymers are those compositions which are reactive with hydroxy and/or carboxylic acid groups. Examples of such cross-linking agents are polyisocyanates (typically di-and/or triisocyanates) polyepoxides and aminoplast resins. Particularly preferred cross-linking agents are the aminoplast resins.

The polyisocyanates when reacted with hydroxyl bearing polyester or polyether or acrylic polymers will yield urethane films useful in the process of this invention in both the base coat and topcoat. The isocyanate (—N=C=O)—hydroxyl (—OH) reaction takes place readily at room temperature, so that ambient and low temperature cure is possible.

Among other resins useful in the base coat are those commonly known as alkyd resins which are defined to include fatty acid or oil containing esterification products. The methods for preparing these resins are well known in the art. The preferred alkyd resins useful in this invention are those containing from about 5 to about 65 weight percent of a fatty acid or oil and having an hydroxyl equivalent to carboxy equivalent ratio of from about 1.05 to 1.75. Alkyd resins having less than about 5% fatty compound are classified as the "oil-less" alkyd resins of polyester resins described hereinafter. On the other hand, alkyd resins containing greater than 65% of a fatty compound exhibit poor baking properties, poor chemical resistance and unsatisfactory adhesion to either the base coat or the substrate. When the hydroxyl to carboxy equivalent ratio is less than about 1.05 gelation can result during polymer preparation while resins prepared having a ratio in excess of 1.75 have low molecular weights and therefore poor chemical resistance. These alkyd resins can also be used as the topcoat of this invention. When this is the case it is preferred that the oil or fatty acid portion of the alkyd resin contain a light colored baking oil or fatty acid such as coconut or dehydrated castor oils or fatty acids. Furthermore, when these resins are used as topcoats they can be reacted with various acrylic or ethylenically unsaturated monomers as described above to produce vinyl modified alkyd resins.

Curing of these alkyd resins can be accomplished by blending with any of the previously described cross-linking agents in the same weight ratios as are used with carboxy-hydroxy copolymers.

Included among the various fatty acids and oils useful in preparing these alkyd resins are the fatty acids derived from the following oils: castor, dehydrated castor, coconut, corn, cottonseed, linseed, oticica, perilla, poppyseed, safflower, soybean, tung oil, etc., and the various rosins containing tall oil fatty acids. Useful polyols include the various glycols, such as ethylene glycol, propylene glycol, neopentyl glycol, butylene glycol, 1,4-butanediol, hexylene glycol, 1,6-hexanediol, the polyglycols such as diethylene glycol or triethylene glycol, etc.; the triols such as glycerine, trimethylol ethane, trimethylol propane, etc., and other higher functional alcohols such as pentaerythritol, sorbitol, mannitol, and the like. Acids useful in preparing the alkyd resins of this invention include mono-fuctional acids such as rosin acids, benzoic acid, p-tert-butyl benzoic acid and the like: the polyfunctioal acids such as adipic acid, azelaic acid, sebacic acid, phthalic acid or anhydride, isophthalic acid, terephthalic acid, dimerized and polymerized fatty acids, trimellitic acid, and the like.

Yet another useful base coat is prepared using nonaqueous dispersions such as are described in U.S. Pat. Nos. 3,050,412; 3,198,759; 3,232,903; and 3,255,135. Typically these dispersions are prepared by polymerizing a monomer such as methyl methacrylate in the presence fo a solvent in which polymers derived from the above monomer are insoluble and a precursor which is soluble in the solvent. Nonaqueous dispersions can have a relative solution viscosity as previously defined of about 1.05 to 3.0. Dispersions having a relative solution viscosity in excess of about 3.0 are difficult to spray and have high coalescence temperatures while dispersions with a relative solution viscosity less than about 1.05 have poor chemical resistance, durability and mechanical properties. The monomers useful in preparing the above-dispersed copolymers or hompolymers are those listed previously as useful in forming the carboxyhydroxy acrylic copolymers.

In another instance the base coat film can be produced from resins known as polyesters or "oil-less" alkyd resins. These resins are prepared by condensing nonfatty containing polyols and polyacids. Included among the useful polyacids are isophthalic acid, phthalic acid or anhydride, terephthalic acid, maleic acid or anhydride, fumaric acid, oxalic acid, sebacic acid, azelaic acid, adipic acid, etc. Mono basic aids such as benzoic, p-tert-butylbenzoic and the like can also be utilized. Among the polyalcohols are the diols or glycols such as propylene glycol, ethylene glycol, bytylene glycol, 1,4-butanediol, neopentyl glycol, hexylene glycol, 1,6-hexanediol, and the like; the triols such as trimethylolethane, trimethylolpropane and glycerine and various other higher functional alcohols such as pentaerythritol.

As discussed above, a water dispersible film forming resin such as a water dispersible non-ionic polyurethane resin of the type disclosed in U.S. Pat. No. 4,794,147, a water dispersible anionic polyurethane resin of the type disclosed in U.S. Pat. No. 4,791,168, or a water dispersible acrylic resin of the type disclosed in U.S. Pat. Nos. 4,403,085 and 4,518,724 is mixed with an aminoplast resin, polyisocyanate, or other suitable cross-linking agent, a suitable grind resin, pigments, one or more rheology control agents if desired, water, and a small amount of organic solvent if needed. Other agents may be included such as various fillers, surfactants, plasticizers, stabilizers, wetting agents, dispersing agents, defoamers, adhesion promoters, and catalysts in minor amounts.

Suitable water-borne film-forming resins and resin dispersions are anionic polyurethane resins and dispersions and nonionic polyurethane resins and resin dispersions of the types described in U.S. Pat. Nos. 4,791,168 and 4,794,147, the contents of which are incorporated herein by reference. Water-borne film-forming resins and resin dispersions based upon acrylic monomers including acrylic acid, methacrylic acid, and alkyl and hydroxyalkyl esters of acrylic and methacrylic acid of the types described in U.S. Pat. Nos. 4,403,085 and 4,518,724 may also be employed in preparing coating compositions of the present invention.

Application of the Coating Compositions

The basecoat compositions containing the surface modified micaceous particulates of the present invention are applied to a metal or plastic substrate in one or more coats using, for example, an air atomizer (Binks Model 60) spray gun, available from the Binks manufacturing Corporation, Franklin Park, Ill.), or by using other conventional spray methods known in the art.

After the basecoat layer containing the surface modified mica particulates has been applied, it may be heated at a temperature and for a time sufficient to cure it to a hard, durable finish. Typically temperatures of about 150° F. (66° C.) and 300° F. (149° C.) and times ranging between about 10 minutes to about 60 minutes suffice. Alternatively, subsequent coating layers may be applied over the uncured basecoat layer. In the latter case, the basecoat layer may be flash dried at a temperature sufficient to remove a portion of the solvent, but below that sufficient to cure the applied coating, typically temperatures within the range of from room temperature to about 145° F. (63° C.). After the first basecoat layer is deposited, a second and subsequent layers of basecoat, if needed or desired, can be deposited over the first either with or without curing or flash drying.

A clear, transparent top coat layer may be subsequently applied over the last base coat layer. Any known unpigmented or transparently pigmented coating agent is, in principle, suitable for use as the top coat material.

The clear coat may be applied over the uncured or previously cured base coat layer(s). When the clear topcoat is applied over a flash-dried, uncured basecoat layer or layers, the multi-layer coating is then baked to cross-link and cure the polymeric materials and to drive the small amount of residual water and/or solvent from the coating layer(s). This baking step generally involves the heating of the coated substrate for periods of from about 10 to about 60 minutes and temperatures ranging between about 150° F. (66° C.) and 300° F. (149° C.). The baking step cures the multi-layer coating to a hard, durable film.

During curing of the basecoat film which contains the surface-modified micaceous particulates, the free hydroxyl functionality of the pendant surface-modifying groups on the micaceous particles reacts with the cross-linking agent(s) in the coating composition. The result is the chemical bonding of the micaceous particles into the cured film of the coating. This chemical bonding is believed to be the result of attachment of the surface-modifying group at one end to the mica surface through the silicon functionality, and at the other end to the cured resin film through the hydroxyl groups and cross-linking agent.

The resulting basecoat films are more durable and resistant to delamination at the mica/intra-basecoat film interfaces. This increased durability for cured films in accordance with the present invention was tested using the ASTM D 3359-83 "Standard Methods for Measuring Adhesion by Tape Test." Steel test panels which had been sprayed with coating compositions of the present invention, as well as similar coatings which lacked the surface treatment of the incorporated mica particulates, were cured to form hard films. The panels were then scored or scribed with an "X". A strip of 3M Type 898 tape (3M Co., Minneapolis, Minn.) was applied over the scoring and pressed into place. The tape was then removed from the panel and the degree of adhesion of the coating film was assessed. In every case, those panels containing the surface treated mica particulates exhibited considerably less delamination of the coating than did the corresponding panels which lacked the surface treatment of the mica particulates.

The following representative Examples are provided to enable those skilled in the art to practice this invention. However, these Examples are merely illustrative and are not to be read as limiting the scope of the invention as defined by the appended claims.

EXAMPLE 1

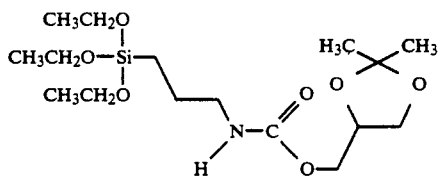

3-(Triethoxysilyl)propyl isocyanate (76.9 g, 0.311 mol) and glycerol isopropylidene ketal (45.4 g, 0.344 mol, available as "solketal" from Aldrich Chemical Co., Milwaukee, Wis.) were charged to a reaction vessel fitted with a stirrer and condensor. A small amount of dibutyl tin dilaurate was also added to the flask contents. The mixture was heated to about 118° C. and maintained at 118°–120° C. for a period of about six hours. At the end of this time, infrared analysis indicated the absence of isocyanate functionality and the reaction was halted. The mixture was cooled and the product collected for use.

EXAMPLE 2

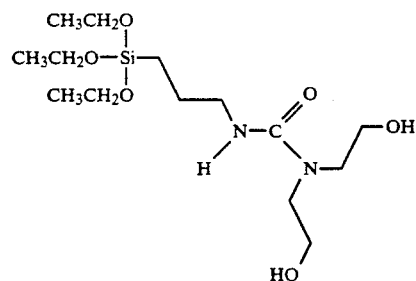

3-Triethoxysilyl)propyl isocyanate (77.9 g, 0.315 mol) was placed in a reaction vessel fitted with a stirrer and condensor. Diethanolamine (35.7 g, 0.340 mol) was slowly added over a period of about one hour. The mixture was stirred without heating while the termperature rose to about 43° C. and then subsided. When the exothermic reaction had ceased, the mixture was heated to 90° C. for one hour, after which infrared analysis indicated the absence of isocyanate functionality. The reaction mixture was cooled and the product collected for use.

EXAMPLE 3

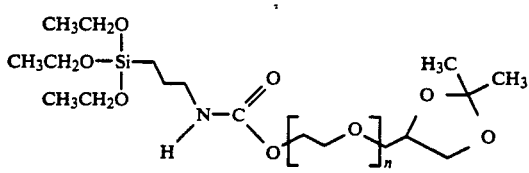

3-(Triethoxysilyl)propyl isocyanate (59.9 g, 0.242 mol) and solketal terminated poly(ethylene oxide) (408.2 g, 0.272 mol, average molecular weight about 1500 Daltons, available from BASF Corporation, Chemicals Division, Parsippany, N.J.) were placed, together with a small amount of dibutyl tin dilaurate, in a reaction vessel fitted with a stirrer and condensor. The mixture was heated to about 118° C. and the mixture was maintained at 118°–120° C. for a period of about six hours. At the end of this time, infrared analysis indicated the absence of isocyanate functionality, and the reaction was halted. The reaction mixture was cooled and the product collected for use.

EXAMPLE 4

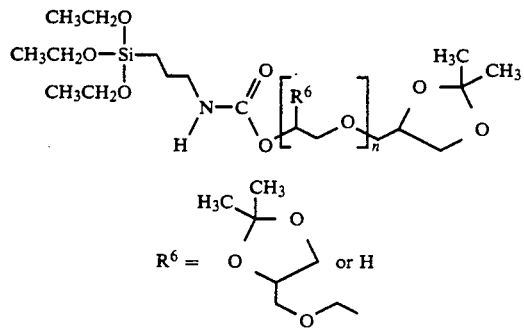

3-(Triethoxysilyl)propyl isocyanate (36.1 g, 0.242 mol) and poly(ethylene oxide) which was a solketal terminated copolymer of ethylene oxide and ethylene oxide functionalized with solketal groups (198.3 g, 0.147 mol, average molecular weight about 1350 Daltons, available from BASF, Corporation, Chemicals Division, Parsippany, N.J.) were placed, together with a small amount of dibutyl tin dilaurate, in a reaction vessel fitted with a stirrer and condensor. The mixture was heated to about 150° C. and then allowed to cool to 110° C., after which the temperature was maintained at 110°–115° C. for a period of about six hours. At the end of this time, infrared analysis indicated the absence of isocyanate functionality, and the reaction was halted. The reaction mixture was cooled and the product collected for use.

EXAMPLE 5

Water-Borne Coating Composition

A coating composition was prepared which contained iron oxide encapsulated mica prepared in accordance with the present invention above.

Black Tint Pigment

A black tint formulation was prepared by mixing 25.42 parts by weight of an anionic polyurethane resin, 15.35 parts by weight Cymel® 327 methylated melamine-formaldehyde resin, 0.08 parts by weight dimethylethanolamine, and 6.29 parts by weight Monarch 900 carbon black (Cabot Corporation, 125 High Street, Boston, Mass. 02110). To this mixture were then added 45.26 parts by weight anionic polyurethane resin and 7.6 parts by weight deionized water.

The anionic polyurethane resin was prepared according to the teachings of U.S. Pat. No. 4,791,168, the contents of which are incorporated herein by reference.

Red Pigment Paste #1

A red pigment paste was prepared by mixing 21 parts by weight anionic polyurethane resin, 5.91 parts by weight Cymel® 327 methylated melamine-formaldehyde resin, and 7.68 parts by weight C.I. Pigment Red 179. After stirring this mixture for thirty minutes, 54.89 parts by weight anionic polyurethane resin and 8.52 parts by weight deionized water were added with mixing. The anionic polyurethane resin was prepared in accordance with the teachings of U.S. Pat. No. 4,791,168.

Red Pigment Paste #2

A red pigment paste was prepared by mixing 24.02 parts by weight anionic polyurethane resin, 12.34 parts by weight Cymel® 327 methylated melamine-formaldehyde resin, 3.61 parts by weight high acid value acrylic grind resin, and 21.65 parts by weight red transparent iron oxide pigment. After stirring this mixture for thirty minutes, 30.91 parts by weight anionic polyurethane resin and 7.47 parts by weight deionized water were added with mixing. The anionic polyurethane resin was prepared in accordance with the teachings of U.S. Pat. No. 4,791,168.

Red Pigment Paste #3

A red pigment paste was prepared by mixing 24.14 parts by weight anionic polyurethane resin, 6.57 parts by weight Cymel® 327 methylated melamine-formaldehyde resin, and 1.72 parts by weight high acid value acrylic grind resin for ten minutes. After this time, 7.57 parts by weight of C.I. Pigment Red 202 were added with stirring. The resulting mixture was stirred for thirty minutes, after which time 60 parts by weight anionic polyurethane resin were added and the resulting mixture stirred for one hour. The anionic polyurethane resin was prepared in accordance with the teachings of U.S. Pat. No. 4,791,168.

Mica Pigment Dispersion

Surface modified iron oxide encapsulate mica particles (23.21 parts by weight), prepared in accordance with Example 12 above, was slurried into 52.21 parts by weight of a branched polyester resin. The resin solution was prepared in accordance with U.S. Pat. No. 4,791,168.

The resin dispersion was stirred vigorously enough to form a vortex and the surface-modified mica was slowly added into the vortex. When the addition was complete, 15.11 parts by weight of a 5% aqueous solution of dimethylethanolamine were added. (All parts by weight are based on 100 parts by weight of the total mica dispersion, the balance comprising ethylene glycol monobutyl ether.)

| Coating Composition | |
|---|---|
| Ingredient | Parts by Weight |
| 1. 2% Dispersion of Laponite RD | 28.58 |

-continued

| Coating Composition | |
|---|---|
| Ingredient | Parts by Weight |
| in water | |
| 2. Cymel ® 327 Methylated melamine formaldehyde resin | 2.02 |
| 3. Ethylene glycol monobutyl ether | 0.50 |
| 4. Non-ionic polyurethane resin dispersion | 25.38 |
| 5. Black tint | 2.00 |
| 6. Red Pigment Paste #1 | 12.90 |
| 7. Red Pigment paste #2 | 7.60 |
| 8. Red pigment paste #3 | 5.35 |
| 9. Treated mica | 3.68 |
| 10. Ethylene glycol monobutyl ether | 4.49 |
| 11. Branched polyester resin | 5.25 |
| 12. 5% Aqueous dimethylethanolamine | 2.25 |
| | 100.00 |

Components 2 and 3 were premixed, and then added to component 1 with rapid stirring. To this mixture were then added, successively with rapid stirring, components 4–8. Components 9–12 were premixed and then added to the mixture with stirring. After mixing of all components, stirring was continued for about one hour, after which the coating composition was placed in a container and capped for later use.

The invention has been described in detail with particular reference to preferred embodiments thereof, but it will be understood that variations and modifications can be affected within the spirit and scope of the invention as defined by the claims appended hereto.

We claim:

1. A compound for use in the surface-modification of micaceous particulates in coating compositions comprising a compound having the formula

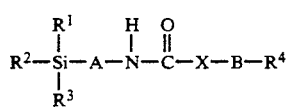

wherein
R$^1$, R$^2$, and R$^3$ may be the same or different and are selected from
  alkyl of from one to ten carbon atoms,
  alkoxyl of from one to ten carbon atoms,
  alkoxylalkoxyl of from two to ten carbon atoms,
  alkanoyloxy of from two to ten carbon atoms, or
  halogen,
with the proviso that R$^1$, R$^2$, and R$^3$ may not all be alkyl;
A is a divalent radical selected from
  straight or branched alkylene of from one to twelve carbon atoms,
  phenylene, or
  phenylene substituted with
    halogen,
    alkyl of from one to four carbon atoms, or
    alkoxyl of from one to four carbon atoms;
X is a divalent radical selected from —O— or —NH—;
B is a direct valence bond or is a divalent group having the formula

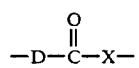

wherein D is a residue derived from the hypothetical removal of the two isocyanate groups from a diisocyanate molecule, and X is a divalent group selected from —O— and —NH—;

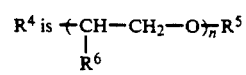

wherein
n is an integer of from zero to one thousand,
R$^6$ is hydrogen, alkyl of from one to eight carbon atoms, or

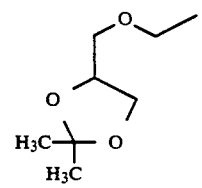

R$^5$ is selected from
  polyols having at least one hydroxyl group, and
  blocked polyols wherein said hydroxy groups are blocked by hydroxy protecting groups.

2. A compound in accordance with claim 1 wherein B is a direct valence bond.

3. A compound as defined by claim 1 wherein B is a divalent group having the formula

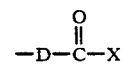

where D is a diisocyanate moiety derived from the hypothetical removal of the two isocyanate functional groups from a diisocyanate molecule, and X is —O— or —NH—.

4. A compound as defined by claim 2 having the formula

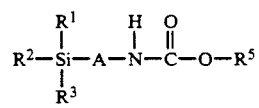

wherein A, R$^1$, R$^2$, R$^3$, and R$^5$ are as defined therein.

5. A compound as defined by claim 2 having the formula

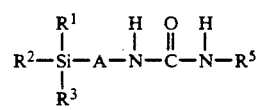

wherein A, R$^1$, R$^2$, R$^3$, and R$^5$ are as defined therein.

6. A compound as defined by claim 2 having the formula

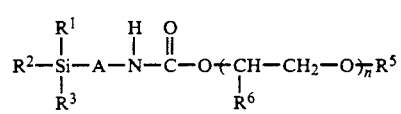

wherein A, R$^1$, R$^2$, R$^3$, R$^5$, R$^6$, and n are as defined therein.

7. A compound as defined by claim 2 having the formula

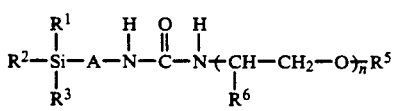

wherein A, R¹, R², R³, R⁵, R⁶, and n are as defined therein.

8. A compound as defined by claim 3 having the formula

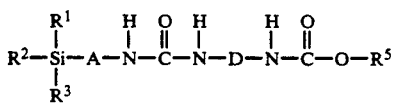

wherein A, D, R¹, R², R³, and R⁵, are as defined therein.

9. A compound as defined by claim 3 having the formula

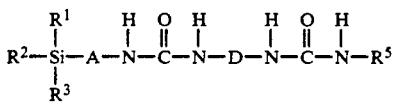

wherein A, D, R¹, R², R³, and R⁵, are as defined therein.

10. A compound as defined by claim 3 having the formula

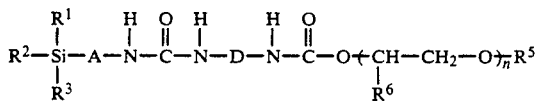

wherein A, D, R¹, R², R³, R⁵, R⁶ and n are as defined therein.

11. A compound as defined by claim 3 having the formula

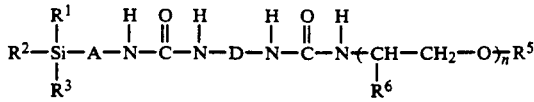

wherein A, D, R¹, R², R³, R⁵, R⁶, and n are as defined therein.

12. A compound as defined in claim 1 wherein R¹, R², and R³ are selected from alkoxyl of from one to ten carbon atoms.

13. A compound as defined by claim 3 wherein the group D is a divalent group selected from
methylene,
ethylene, or
straight chain or branched chain alkylene of from three to six carbon atoms.

14. A compound as defined by claim 3 wherein the group D is a divalent group selected from cycloalkylene and substituted cycloalkylene of from five to twelve carbon atoms.

15. A compound as defined by claim 3 wherein the group D is a divalent group selected from phenylene, substituted phenylene, biphenylene, substituted biphenylene, diarylalkylene, naphthylenyl, and substituted naphthalenyl.

16. A compound as defined by claim 1 wherein n is 0.

17. A compound as defined by claim 1 wherein n is an integer of from 1 to 1000.

18. A compound as defined by claim 6 wherein n is an integer of from 1 to 1000.

19. A compound as defined by claim 7 wherein n is an integer of from 1 to 1000.

20. A compound as defined by claim 10 wherein n is an integer of from 1 to 1000.

21. A compound as defined by claim 11 wherein n is an integer of from 1 to 1000.

* * * * *